United States Patent
Olah et al.

(10) Patent No.: US 8,697,759 B1
(45) Date of Patent: Apr. 15, 2014

(54) EFFICIENT, SELF SUFFICIENT PRODUCTION OF METHANOL FROM A METHANE SOURCE VIA OXIDATIVE BI-REFORMING

(71) Applicant: Univeristy of Southern California, Los Angeles, CA (US)

(72) Inventors: George A. Olah, Beverly Hills, CA (US); G. K. Surya Prakash, Hacienda Heights, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 13/791,778

(22) Filed: Mar. 8, 2013

Related U.S. Application Data

(60) Provisional application No. 61/711,610, filed on Oct. 9, 2012.

(51) Int. Cl.
    *C07C 27/06* (2006.01)

(52) U.S. Cl.
    USPC .......................................... 518/704

(58) Field of Classification Search
    None
    See application file for complete search history.

(56) References Cited

U.S. PATENT DOCUMENTS

| | | | |
|---|---|---|---|
| 3,993,457 | A | 11/1976 | Cahn et al. |
| 4,093,029 | A | 6/1978 | Weisz et al. |
| 4,395,495 | A | 7/1983 | Cummings |
| 4,618,732 | A | 10/1986 | Gesser et al. |
| 4,640,766 | A | 2/1987 | Post et al. |
| 5,342,702 | A | 8/1994 | MacGregor |
| 5,599,638 | A | 2/1997 | Surampudi et al. |
| 5,767,165 | A | 6/1998 | Steinberg et al. |
| 5,856,585 | A | 1/1999 | Sanfilippo et al. |
| 7,132,183 | B2 | 11/2006 | Galloway |
| 7,605,293 | B2 | 10/2009 | Olah et al. |
| 7,608,743 | B2 | 10/2009 | Olah et al. |
| 7,705,059 | B2 | 4/2010 | Olah et al. |
| 7,795,175 | B2 | 9/2010 | Olah et al. |
| 2004/0034255 | A1 | 2/2004 | Shoji et al. |
| 2008/0319093 | A1 | 12/2008 | Olah et al. |
| 2009/0264543 | A1* | 10/2009 | Xu et al. ........................ 518/728 |

FOREIGN PATENT DOCUMENTS

| | | |
|---|---|---|
| EP | 0 159 759 | 10/1985 |
| GB | 1 545 329 | 5/1979 |
| WO | WO 2006/113294 | 10/2006 |
| WO | WO 2007/014487 | 2/2007 |
| WO | WO2012045373 A1 | 12/2012 |

OTHER PUBLICATIONS

International Search Report and Written Opinion of the International Searching Authority, Application No. PCT/US2008/067480, Oct. 1, 2008.
International Search Report, Application No. PCT/US2008/067462, Oct. 1, 2008.
Non-Final Office Action, U.S. Appl. No. 12/941,773, dated Feb. 18, 2011.
Advisory Action Office Action, U.S. Appl. No. 12/941,773, dated Nov. 4, 2011.
Final Office Action, U.S. Appl. No. 12/941,773, dated Jul. 26, 2011.
Non-Final Office Action, U.S. Appl. No. 11/850,501, dated Mar. 19, 2010.
Final Office Action, U.S. Appl. No. 11/850,501, dated Aug. 27, 2010.
International Search Report and Written Opinion, PCT/US2013/058469, mailed Nov. 7, 2013.
A.E.C. Palmqvist et al., "Total oxidation of methane over doped nanophase cerium oxides", Catalysis Letters, vol. 56, pp. 69-75 (1998).

* cited by examiner

*Primary Examiner* — Sudhakar Katakam
(74) *Attorney, Agent, or Firm* — Winston & Strawn LLP

(57) ABSTRACT

A method for producing methanol from a methane source such as methane from natural (shale) gas by first reacting one equivalent of methane with oxygen from the air to result in complete combustion to produce carbon dioxide and water in a molar ratio of 1:2; then conducting a bi-reforming process with a mixture of methane:carbon dioxide:water having a ratio of 3:1:2 to produce metgas, a mixture of hydrogen and carbon monoxide having a molar ratio of 2:1 to 2.1:1; and finally converting metgas exclusively to methanol. The thus produced methanol can be dehydrated to form dimethyl ether, with water produced being recycled back to the bi-reforming process, if necessary.

18 Claims, No Drawings

EFFICIENT, SELF SUFFICIENT PRODUCTION OF METHANOL FROM A METHANE SOURCE VIA OXIDATIVE BI-REFORMING

BACKGROUND

Although fossil fuels still have a wide application and high demand, they have limitations due to their finite reserves. Also, the combustion of fossil fuels produces carbon dioxide, which contributes to global warming.

With the development of various large natural (shale) gas sources in many parts of the world and with the existence of other methane sources such as coal bed methane, methane hydrates, etc., the availability of extensive methane reserves is assured at least for this century. The conversion of natural (shale) gas into liquids, preferentially to methanol used for transportation fuels and source material for varied essential chemical products, is of great practical significance (*Beyond Oil and Gas: The Methanol Economy*, G. A. Olah, A. Goeppert and G. K. S. Prakash, $2^{nd}$ Edition, Wiley-VCH, Weinheim, 2009). Currently, widely practiced steam reforming processes of methane generate syngas, $CO:H_2$ with a ratio of 1:3. Additionally, dry reforming with carbon dioxide provides $CO:H_2$ in a 1:1 ratio. To manage the needed energy requirement (endothermicity) of the steam reforming, several processes including tubular as well as autothermal reforming (ATR) using partial combustion have been developed and widely used (*Concepts in Syngas Manufacture*, J. Rostrup-Nielson and L. J. Christiansen, Imperial College Press, London, 2011) to produce varying syngas compositions. In ATR, partial oxidation of methane with oxygen is combined with the steam reforming in the same reactor. These processes involve multiple steps to adjust the needed syngas ratio, however, and also produce significant amounts of carbon dioxide or other oxidation byproducts, which need to be separated or disposed. A $CO:H_2$ ratio of 1:2 is not produced a single step either in ATR processes or in any of the other reforming processes.

The present invention discloses a new way to utilize methane or natural (shale) gas sources to produce methanol and derived products to be used in the context of the "Methanol Economy". Fossil fuel sources such as petroleum oil, natural gas and coal can be converted by known processes, including those disclosed in the patent applications of the present inventors, into methanol and dimethyl ether by bi-reforming, involving chemical recycling of carbon dioxide, the final product of their combustion use. Methanol and dimethyl ether are used as transportation fuels, as substitutes for gasoline and diesel fuel in ICE-powered vehicles with some necessary modifications to the existing engines and fuel systems, as well as in fuel cells. The storage and use of methanol, in contrast with hydrogen, does not require new infrastructure such as expensive pressurization and liquefaction. Because methanol is a liquid, it can be easily handled, stored, distributed and used in vehicles. It is also an ideal hydrogen carrier for fuel cells using a reformer and can be used in direct oxidation methanol fuel cells (DMFC). Dimethyl ether although a gas at room temperature, can be easily stored under modest pressure and used effectively as substitute for diesel fuels, liquefied natural gas (LNG) liquefied petroleum gas (LPG) and household gas.

In addition to use as fuels, methanol, dimethyl ether and their derived products have significant applications and uses. They are starting materials for varied chemical products. They can be catalytically converted into olefins primarily ethylene and propylene and their polymers. They are thus convenient starting materials for synthetic hydrocarbons and their products further replacing oil.

Methanol can also be used as a source of single cell proteins (SCP). SCP refers to a protein produced by a microorganism, which degrades hydrocarbon substrates while gaining energy. The protein content depends on the type of microorganism, e.g., bacteria, yeast, mold, etc. SCP's have varied uses, including as food and animal feed.

Considering the wide uses of methanol and dimethyl ether, it is clearly desirable to have improved and efficient new methods for producing them.

SUMMARY OF THE INVENTION

The present invention discloses a new efficient, self sufficient, environmentally friendly carbon and energy neutral and economic conversion of fast developing extensive methane, natural (shale) gas and other methane sources through oxidation and bi-reforming to produce exclusively metgas (i.e., a specific syngas having an approximately 2:1 mole ratio of CO and $H_2$), which is then converted exclusively to methanol and derived products thereof to be used as fuels, energy storage and starting materials for varied synthetic hydrocarbons and chemical products produced therefrom.

In particular, the invention relates to a method of producing methanol from a source of methane, by reacting one equivalent of methane from a methane source with oxygen from the atmosphere under conditions sufficient to result in complete combustion to produce a mixture of carbon dioxide and water in a molar ratio of about 1:2 and to generate heat for subsequent use in the method; combining the carbon dioxide and water produced from the combustion with three equivalent amount of methane from the methane source to produce a mixture of methane:carbon dioxide:water having a molar ratio of 3:1:2; conducting a single-step bi-reforming reaction with the mixture of methane:carbon dioxide:water and with the heat generated from the complete combustion to form only carbon monoxide and hydrogen as follows:

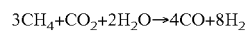
$$3CH_4 + CO_2 + 2H_2O \rightarrow 4CO + 8H_2$$

to exclusively produce metgas having a mixture of hydrogen and carbon monoxide at a molar ratio of between 2:1 and 2.1:1; and converting the metgas under conditions sufficient to exclusively form methanol, as follows:

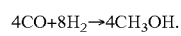
$$4CO + 8H_2 \rightarrow 4CH_3OH.$$

Preferably, the sole reactants for the method are the methane from the methane source and the oxygen from the atmosphere. The heat of combustion of the methane provides most or all of energy needed for conducting the subsequent bi-reforming reaction.

In this method, the methane source needed for providing the methane for combining with the carbon dioxide and water is obtained preferentially from a natural (shale) gas thus utilizing only the natural (shale) gas and the oxygen from the atmosphere as the sole reactants for combustion and carrying out the method. The source of methane may include coal bed methane, methane hydrates, biogas derived methane, or any other industrial or natural sources that contain methane, used either alone or in any combination including combinations with natural (shale) gas.

Alternatively, the method further comprises separating the methane from other components of the natural (shale) gas or other methane source to provide the methane for combustion and separating the oxygen from the atmosphere for use in the method. When using natural or shale gas, the feed can be easily adjusted to the required ratios and if needed additional water from any source can be added. The feed, if necessary, is also purified from $H_2S$, excess $CO_2$ and/or other impurities.

The bi-reforming reaction is highly endothermic. Preferably, the heat of combustion of one equivalent of methane with oxygen provides all of the energy needed for conducting the bi-reforming reaction. If necessary, the provided energy can be coupled with energy from the exothermic methanol synthesis step making the overall process exothermic or close to thermo-neutral. If desired, additional energy for the bi-reforming reaction can be provided from one or more alternative or green energy sources.

The bi-reforming reactions are typically carried out over a catalyst at a temperature between about 800° C. and 1100° C. and a pressure of 5 to 40 bar, wherein the catalyst comprises V, Ti, Ga, Mg, Cu, Ni, Mo, Bi, Fe, Mn, Co, Nb, Zr, La or Sn, or oxides thereof in the form of a single metal catalyst, a single metal oxide catalyst, a mixed catalyst of a metal and a metal oxide deposited on a suitable support of high surface area, with the support comprising silica, alumina or their combination and with the catalyst being thermally activated under hydrogen.

The combustion of natural (shale) gas may also take place in power plants or other plants wherein the hot exhaust mixture of mixture of carbon dioxide and water (steam) are subsequently utilized in the production of metgas. If desired, the methane obtained from the methane source can simply be added to the power plant exhaust for providing the metgas mixture for the bi-reforming reaction.

In another embodiment, the method further comprises dehydrating all or a portion of the methanol to dimethyl ether and recycling, if needed, the water from the dehydration to the bi-reforming reaction.

The present invention more generally relates to a method of exclusively producing methanol from methane and oxygen of the atmosphere (air) as the only reactants, which comprises reacting methane with oxygen under conditions sufficient to result in combustion of methane to produce a mixture of carbon dioxide and steam in a molar ratio of about 1:2 and generate heat; combining the carbon dioxide and water produced from the combustion with a sufficient additional amount of the methane to produce a mixture of methane: carbon dioxide:water (steam) having a molar ratio of 3:1:2; conducting bi-reforming reactions with the mixture of methane:carbon dioxide:water and the heat generated from the combustion by to form only carbon monoxide and hydrogen; combining carbon monoxide and hydrogen produced from the bi-reforming reaction to produce a mixture of hydrogen and carbon monoxide having a molar ratio of 2:1 to 2.1:1; and converting the mixture of hydrogen and carbon monoxide under conditions sufficient to exclusively form methanol. The sole reactants for the method are the methane from any source and the oxygen of the atmosphere (air) and wherein the heat of combustion of the methane provides the energy needed for conducting the bi-reforming reactions.

Significantly, the invention relates to exclusive overall reaction of methane and oxygen of the atmosphere (air) as the only reactants for producing methanol with no waste or byproducts.

DETAILED DESCRIPTION OF THE PREFERRED EMBODIMENTS

The invention preferably relates to the conversion of methane or natural (shale) gas to methanol and/or dimethyl ether. Methanol and dimethyl ether thus produced find utility in numerous applications on what is now called the "Methanol Economy", such as fuels, energy storage and starting materials for varied synthetic hydrocarbon and products produced therefrom. Specifically, the present invention provides a novel self sufficient and economic method to convert methane or, natural (shale) gas or other methane sources selectively into methanol through the production of metgas (approximately 2:1 mol ratio of CO and $H_2$) to produce methanol.

Natural gas has varied compositions depending on locations with methane predominating frequently accompanied by carbon dioxide and harmful $H_2S$ gas. Natural gas trapped in shale formations along with homologues is called shale gas. Shale gas can be divided into dry and wet shale gas. The former is practically pure methane (>98%), which can be used directly in the methods of the invention. The latter contains about 70% methane and 30% higher hydrocarbon homologues such as ethane and propane. Ethane and propane, after being separated from methane, can be dehydrogenated to ethylene and propylene. Shale gas liquids can also be utilized for other purposes such as producing gasoline range hydrocarbons and other products.

In one typical embodiment, the method of the invention involves the complete combustion of one equivalent methane feed with oxygen to produce carbon dioxide and water. The oxygen can be obtained from air itself containing non-reactive gases such as nitrogen. This combustion is a highly exothermic reaction, with substantial heat generation. Such combustion is commonly practiced in natural gas burning power plants, other industries and in households:

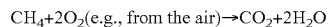
$CH_4+2O_2$(e.g., from the air)$\rightarrow CO_2+2H_2O$

The hot $CO_2$-$2H_2O$ exhaust of the complete combustion of 1 mole equivalent of methane or natural (shale) gas is then combined with 3 mole equivalent of methane or natural (shale) gas needed for subsequent use in the bi-reforming step to produce exclusively metgas (CO:$H_2$ in 1:2 ratio) as disclosed in the present inventors' U.S. Pat. Nos. 7,906,559 and 8,138,380, the entire contents of each of which are incorporated herein by reference thereto. Thus, the reaction is:

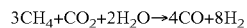
$3CH_4+CO_2+2H_2O\rightarrow 4CO+8H_2$

A skilled practitioner is aware of how to configure equipment and process streams to provide the necessary amounts of methane or natural (shale) gas to satisfy the stoichiometry needed to carry out the reactions of the process of the present invention. The feed is also purified when needed from excess of $CO_2$ and $H_{2S}$ and other impurites.

The bi-reforming process utilizes a specific combination of steam ($H_2O$) and dry ($CO_2$) reforming in a single step. The bi-reforming process can be conducted by reacting methane or natural (shale) gas, steam and carbon dioxide in the specific molar ratio of 3:2:1 over a catalyst such as mixed metal-metal oxide catalyst at a temperature between about 800° C. and 1100° C., preferably from about 800° C. to about 850° C., and a pressure of 5 to 40 bar sufficient to produce metgas, namely a syn-gas mixture of carbon monoxide/hydrogen (CO/$H_2$) in a molar ratio of about 2:1, preferably between 2:1 and 2.1:1, and most preferably about 2.05:1; and subsequently further sufficient to convert such mixture of $H_2$ and CO exclusively to methanol. Advantageously, the mixture of reactants is treated without separation of its components to convert substantially all the reactants to methyl alcohol without any by-products. Preferably, un-reacted starting or intermediate products are recovered and recycled in a subsequent reaction step. This overall process achieves high selectivity in methanol with practically applicable high yields.

To carry out the bi-reforming step, a catalyst or combination of catalysts can be used. These catalysts include any suitable metal or metal oxide, including without limitation a metal such as V, Ti, Ga, Mg, Cu, Ni, Mo, Bi, Fe, Mn, Co, Nb, Zr, La or Sn, and corresponding oxides of such metals. These catalysts may be used as a single metal, or a combination of a metal and metal oxide, or a combination of metal oxides, supported on a suitable support such as a high surface area nanostructured oxide support such as fumed silica or fumed alumina. The catalyst is thermally activated for use under hydrogen. By way of example, NiO, metal-metal oxides such as Ni—$V_2O_5$, ($M_2O_3$—$V_2O_5$), and NiO:$V_2O_5$, as well as mixed oxides such as $Ni_2V_2O_7$ and $Ni_3V_2O_8$ can be used. One skilled in the art would appreciate that a number of other related metal and metal oxide catalysts, and their combinations, can also be used. Suitable reactors for the oxidative bi-reforming can be used separating the initial complete combustion from subsequent bi-reforming reaction in single or separate reactors, such as high-pressure continuous flow reactors under the appropriate reaction conditions at suitable temperatures and pressures. Such reactors are familiar to those involved in reforming technologies.

The heat generated from the complete combustion of methane from the natural (shale) gas provides the process energy for the highly endothermic bi-reforming reaction, rendering the overall process exothermic (Scheme-1).

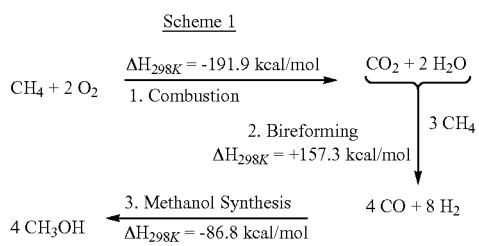

The methods of oxidative bi-reforming process is preferentially conducted in a dual wall tubular flow reactor or heat exchanger, wherein the combustion is conducted in the outer tube to generate heat with the bi-reforming conducted in an inner tube into which the additional amounts of methane are provided (the outer and the inner tube configuration can also be reversed for the reactions). As noted the only reactants needed to carry out the entire process are methane from a suitable source, typically natural (shale) gas, coal bed methane, methane hydrates, biogas derived methane, etc. and oxygen that is preferably obtained from the air (atmosphere) by separation therefrom. Such separation steps are generally known to a skilled artisan (see, e.g., U.S. Pat. No. 7,459,590) and need no further description here.

Accordingly, the initial combustion step should provide sufficient energy for the bi-reforming step while the methanol synthesis provides further energy. If necessary, however, any additional energy needed for the bi-reforming step of the invention can also come from any other suitable energy source, including, but not limited to any alternative energy sources including solar, wind, or atomic energy.

The bi-reforming process produces exclusively metgas, namely, a molar ratio of $H_2$ and CO of about 2 moles hydrogen to 1 mole of carbon monoxide, for the synthesis of methanol in a subsequent step over usual Cu—ZnO or related catalysts in high overall yield.

The significant advantage of the process of the invention for converting methane or natural (shale) gas into methanol is that substantially all of the feed is converted to give metgas, a close to a 2:1 molar ratio of hydrogen and carbon monoxide, which is ideally suited for the subsequent production of methanol. If desired, methanol produced by the process of the invention is converted to dimethyl ether via its dehydration. Dehydration can be achieved over varied catalysts such as dry silica catalyst or a polymeric perfluoroalkanesulfonic acid catalyst at a temperature range of about 100° C. to 200° C. An example of such catalyst is Nafion-H.

This embodiment of the invention can be depicted as:

$$2CH_3OH \rightarrow CH_3OCH_3 + H_2O$$

In a further embodiment, the production of dimethyl ether can also be carried out by the recycling of water formed in the dehydration step into the bi-reforming reaction. In this embodiment, the water formed during the dehydration of methanol, if needed, can be completely reused.

A significant advantage of the process of the invention is that it is a simple self-supporting method for synthesizing methanol from methane of any source via oxidation and bi-reforming using only the oxygen of the air (atmosphere) in the overall exothermic reaction. The process of the invention achieves the long sought-after but never realized goal of converting methane to methanol by inserting a single oxygen atom into the methane or its sources such as shale or natural gas with no byproducts or waste in an exothermic highly economic, efficient and self sufficient process.

One significant feature of the process of the invention is that it is essentially carbon and energy neutral and has very little if any carbon footprint. Thus, a further advantage of the invention is that carbon dioxide is not released into the atmosphere or sequestered but is recycled via its conversion to methanol. For example, in a power plant, after methane in the natural (shale) gas is completely combusted, the resulting carbon dioxide and steam is recovered and used in the bi-reforming reaction for the production of methanol. Also the process is essentially energy neutral adoptable for most and even remote locations.

Presently, the commercial production of methanol uses syngas-based processes including ATR, which utilizes internal partial oxidation for providing the reaction heat but requires adjusting the syngas composition to CO-2$H_2$ and producing unwanted by-products including $CO_2$, thus necessitating carefully controlled conditions as well as additional costly steps. Consequently, modern methanol plants are economic and feasible only with >1 million tonnes/year capacity and represent a multi-billion dollar investment. As the simple and efficient process of the invention achieves extremely significant cost savings, it is possible to operate smaller plants (of ~50,000 t/y capacity), which can be readily scaled up to >1 Mt/y mega plants. As the process of the invention does not need much external energy input or purification of $CO_2$ or water, it is internally self-sufficient and can be used with great flexibility to location. Moreover, the process of the invention, which generates metgas to produce methanol from natural (shale) gas, can also be adapted to produce methanol from the exhausts of natural (shale) gas or even coal or oil burning power plants containing carbon dioxide and steam.

The individual reactions of the process of the invention, namely, the complete combustion of methane or natural (shale) gas with oxygen of the air, the bi-reforming reaction of methane using $CO_2$ and $H_2O$, and the synthesis of methanol from metgas (CO-2$H_2$), are separately known and well proven. Applying the heat generated from the partial oxidation of methane for the reforming process is also known. For example, WO 2007/014487 discloses combining the partial oxidation of methane (POM) with the wet reforming and/or the dry reforming reaction in a single step. Although such "thermoneutral tri-reforming" reaction allows the heat produced in the exothermic partial oxidation of methane to be used in the endothermic steam and dry reforming reactions, the partial oxidation produces a mixture of products, thus necessitating further costly separation process and adjustments to obtain a syngas containing CO and $H_2$ in a molar ratio of 1:2 for the production of methanol. The process of the present invention provides a simple, economic and environmentally benign solution for converting methane or natural (shale) gas exclusively to methanol by conducting the complete combustion of part of methane first and using the products of the complete combustion, i.e., $CO_2$ and $H_2O$, in a molar ratio of 1:2 for the subsequent bi-reforming reaction with methane or natural (shale) gas to produce metgas, which is subsequently used to produce exclusively methanol without requiring separation of products or the addition of energy from external sources.

The process of the invention in its entirety provides a new economic, environmentally carbon neutral and feasible method for the selective and exclusive production of methanol without waste and byproducts, which also has the flexibility of being adjusted to any local condition and available feeds. The process of the invention thus allows the efficient and environmentally friendly and economic processing of methane or natural (shale) gas to methanol and/or dimethyl ether, as well as their derived products.

EXAMPLES

The following examples illustrate the preferred embodiments of the invention without limiting them.

Example 1

One equivalent of methane is subjected to complete oxidation, followed by the bi-reforming process of the effluents with added three equivalents of methane in a suitable double walled flow reactor over metal/metal oxide catalysts of such as NiO at a temperature of about 800° C. to 1100° C., preferentially between 800-850° C. Suitable catalysts also include varied metal and metal oxides such as V, Ti, Ga, Mg, Cu, Ni, Mo, Bi, Fe, Mn, Co, Nb, Zr, or Sn used as single metal, metal oxides or their combination. They can be supported on suitable support, preferentially suitably large nanostructured surface such as fumed silica or alumina and are thermally activated under hydrogen. A preferred catalyst is NiO on fused alumina support. This process provides metgas, the desired mixture of CO and $H_2$.

Example 2

Adjusting the feed mixture to natural (shale) gas or other methane sources in Example 1 to give CO and $H_2$ composition of 2:1 mole ratio (metgas) suitable for the production of methanol. The feed, when needed is also purified from excess $CO_2$, $H_2S$ and other impurites.

Example 3

A metgas mixture of hydrogen and carbon monoxide produced in approximately 2:1 ratio is converted to produce methanol under catalytic reaction conditions using usual copper and zinc oxides or related catalysts.

Example 4

The methanol produced in Example 3 is dehydrated to dimethyl ether using a solid acid catalyst such as Nafion H between 100° C. to 200° C.

Example 5

The water formed during dehydration of methanol to dimethyl ether, if needed, is recycled to be used in the bi-reforming reaction in Example 1.

The invention described and claimed herein is not to be limited in scope by the specific embodiments herein disclosed, as these embodiments are intended as illustrative of several aspects of the invention. Any equivalent embodiments are intended to be within the scope of this invention, as they will become apparent to those skilled in the art from the present description. Such embodiments are also intended to fall within the scope of the appended claims.

What is claimed is:

1. A method of producing methanol from a source of methane, which comprises:
reacting one equivalent of methane from a methane source with oxygen from the atmosphere (air) under conditions sufficient to result in complete combustion to produce a mixture of carbon dioxide and water in a molar ratio of about 1:2 and to generate heat for subsequent use in the method;
combining the carbon dioxide and water produced from the combustion with a three equivalent amount of methane from the methane source to produce a mixture of methane:carbon dioxide:water having a molar ratio of 3:1:2;
conducting a single-step bi-reforming reaction with the mixture of methane:carbon dioxide:water and with the heat generated from the complete combustion to form only carbon monoxide and hydrogen as follows:

$$3CH_4+CO_2+2H_2O \rightarrow 4CO+8H_2$$

to exclusively produce metgas having a mixture of hydrogen and carbon monoxide at a molar ratio of between 2:1 and 2.1:1; and
converting the metgas under conditions sufficient to exclusively form methanol, as follows:

$$4CO+8H_2 \rightarrow 4CH_3OH,$$

wherein the sole reactants for the method are the methane from the methane source and the oxygen from the atmosphere (air).

2. The method of claim 1, wherein the methane source needed for providing the methane for combining with the carbon dioxide and water is obtained from a natural (shale) gas thus utilizing only the natural (shale) gas and the oxygen from the atmosphere as the sole reactants for combustion and carrying out the method.

3. The method of claim 2, which further comprises separating the methane from other accompanying components of the natural (shale) gas such as excess $CO_2$, $H_2S$ and other impurities to provide the methane for combustion and separating the oxygen from the atmosphere (air) for use in the method.

4. The method of claim 1, wherein the source of methane includes coal bed methane, methane hydrates, biogas derived methane or any other source of methane.

5. The method of claim 1, wherein the heat of combustion of one equivalent of methane with the oxygen of the atmosphere (air) provides all of the energy needed for conducting the bi-reforming reactions.

6. The method of claim 1, which further comprises providing additional process energy if needed for the bi-reforming reaction from one or more alternative or green energy sources.

7. The method of claim 1, wherein combustion performed in power plants burning coal or oil wherein heat and the mixture of carbon dioxide and water are collected and are used in the method.

8. The method of claim 7, which further comprises adding the methane to the power plant exhaust for combining with the carbon dioxide and water.

9. The method of claim 1, wherein the bi-reforming reactions are carried out over a catalyst at a temperature between about 800° C. and 1100° C. and a pressure of 5 to 40 bar, wherein the catalyst comprises V, Ti, Ga, Mg, Cu, Ni, Mo, Bi, Fe, Mn, Co, Nb, Zr, La or Sn, or oxides thereof in the form of a single metal catalyst, a single metal oxide catalyst, a mixed catalyst of a metal and a metal oxide deposited on a suitable support of high surface area, with the support comprising silica, alumina or their combination and with the catalyst being thermally activated under hydrogen.

10. The method of claim 1 which further comprises dehydrating all or a portion of the methanol to dimethyl ether and recycling the water from the dehydration to the bi-reforming reaction.

11. A method of exclusively producing methanol from a source of methane and oxygen from the atmosphere as the only reactants which comprises:
    reacting one equivalent of methane from a methane source with oxygen from the atmosphere under conditions sufficient to result in complete combustion to produce a mixture of carbon dioxide and water in a molar ratio of about 1:2 and to generate heat for subsequent use in the method;
    combining the carbon dioxide and water produced from the combustion with a three equivalents of methane from the methane source to produce a mixture of methane:carbon dioxide:water having a molar ratio of 3:1:2;
    conducting a single-step bi-reforming reaction with the mixture of methane:carbon dioxide:water and with the heat generated from the complete combustion to form only carbon monoxide and hydrogen as follows:

$$3CH_4 + CO_2 + 2H_2O \rightarrow 4CO + 8H_2$$

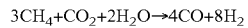

to exclusively produce metgas having a mixture of hydrogen and carbon monoxide at a molar ratio of between 2:1 and 2.1:1; and
    converting the metgas under conditions sufficient to exclusively form methanol, as follows:

$$4CO + 8H_2 \rightarrow 4CH_3OH,$$

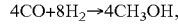

wherein the sole reactants for the method are the methane from the methane source and the oxygen from the atmosphere and wherein the heat of combustion of the methane provides most or all of energy needed for conducting the bi-reforming reaction.

12. The method of claim 11, wherein the methane source needed for providing the methane for combining with the carbon dioxide and water is obtained from a natural (shale) gas thus utilizing only the natural (shale) gas and the oxygen from the atmosphere as the sole reactants for combustion and carrying out the method.

13. The method of claim 12, which further comprises separating and purifying the methane from other components of the natural (shale) gas to provide the methane for combustion and separating the oxygen from the atmosphere for use in the method.

14. The method of claim 11, wherein the source of methane includes coal bed methane, methane hydrates, biogas derived methane or any other industrial or natural sources that contain methane.

15. A method of producing methanol from a source of methane, which comprises:
    reacting one equivalent of methane from a methane source with oxygen under conditions sufficient to result in complete combustion of the methane to produce a mixture of carbon dioxide and water in a molar ratio of about 1:2 and to generate heat for subsequent use in the method;
    combining the carbon dioxide and water produced from the combustion with a three equivalent amount of methane from the methane source to produce a mixture of methane:carbon dioxide:water having a molar ratio of 3:1:2;
    conducting a single-step bi-reforming reaction that combines steam reforming and dry reforming on the mixture of methane:carbon dioxide:water and with the heat generated from the complete combustion of methane to form only carbon monoxide and hydrogen to exclusively produce metgas having a mixture of hydrogen and carbon monoxide at a molar ratio of between 2:1 and 2.1:1; and
    converting the metgas under conditions sufficient to exclusively form methanol,
    wherein the sole reactants for the method are the methane from the methane source and the oxygen.

16. The method of claim 15, wherein the methane source needed for providing the methane for combining with the carbon dioxide and water is obtained from a natural (shale) gas thus utilizing only the natural (shale) gas and oxygen obtained from the atmosphere as the sole reactants for combustion and carrying out the method.

17. The method of claim 16, which further comprises separating and purifying the methane from other components of the natural (shale) gas to provide the methane for combustion and separating the oxygen from the atmosphere for use in the method.

18. The method of claim 15, wherein the source of methane includes coal bed methane, methane hydrates, biogas derived methane or any other industrial or natural sources that contain methane.

* * * * *